(12) United States Patent
Yang et al.

(10) Patent No.: US 12,195,483 B2
(45) Date of Patent: Jan. 14, 2025

(54) PLATINUM COMPLEXES HAVING FERROCENE LIGANDS FOR THE CATALYSIS OF THE ALKOXYCARBONYLATION OF ETHYLENICALLY UNSATURATED COMPOUNDS

(71) Applicant: EVONIK OPERATIONS GMBH, Essen (DE)

(72) Inventors: Ji Yang, Harbin (CN); Matthias Beller, Ostseebad Nienhagen (DE); Ralf Jackstell, Rostock (DE); Robert Franke, Marl (DE)

(73) Assignee: EVONIK OXENO GMBH & CO. KG, Marl (DE)

( * ) Notice: Subject to any disclaimer, the term of this patent is extended or adjusted under 35 U.S.C. 154(b) by 451 days.

(21) Appl. No.: 17/215,075

(22) Filed: Mar. 29, 2021

(65) Prior Publication Data
US 2021/0300957 A1 Sep. 30, 2021

(30) Foreign Application Priority Data
Mar. 30, 2020 (EP) .................................. 20166579

(51) Int. Cl.
*B01J 31/00* (2006.01)
*B01J 31/16* (2006.01)
*C07C 67/38* (2006.01)
*C07F 15/00* (2006.01)
*C07F 15/02* (2006.01)

(52) U.S. Cl.
CPC ........... *C07F 15/02* (2013.01); *B01J 31/1616* (2013.01); *C07C 67/38* (2013.01); *C07F 15/0086* (2013.01); *C07C 2531/16* (2013.01)

(58) Field of Classification Search
None
See application file for complete search history.

(56) References Cited

U.S. PATENT DOCUMENTS

| 2017/0022236 A1 | 1/2017 | Dong et al. |
| 2018/0022773 A1* | 1/2018 | Dong .................. C07F 15/0066 556/144 |
| 2021/0299645 A1 | 9/2021 | Yang et al. |

FOREIGN PATENT DOCUMENTS

| EP | 0 662 467 A1 | 7/1995 | |
| WO | WO 2007/057640 A1 * | 5/2007 | .............. B01J 31/24 |

OTHER PUBLICATIONS

U.S. Appl. No. 17/544,227, filed Dec. 7, 2021, Yang et al.
U.S. Appl. No. 17/544,144, filed Dec. 7, 2021, Schneider et al.
U.S. Appl. No. 17/544,179, filed Dec. 7, 2021, Schneider et al.
U.S. Appl. No. 17/544,254, filed Dec. 7, 2021, Schneider et al.
European Search Report dated Aug. 18, 2020 for European Patent Application No. 20166579.1 (8 pages in German with translation).
Colacot, T. J., et al. Precious Metal-Phosphine Complexes for Homogeneous Catalysis: Synthesis and Characterization of a Complete Series of $Cp_2Fe(PPh_2)_2MX_2$ (M = Pt, Pd; X = Cl, Br, I, Ph). Phosphorous, Sulfur, and Silicon and the related Elements. 1999. pp. 49-52.

* cited by examiner

*Primary Examiner* — Yun Qian
(74) *Attorney, Agent, or Firm* — Smith, Gambrell & Russell, LLP

(57) ABSTRACT

Platinum complexes having ferrocene ligands for the catalysis of the alkoxycarbonylation of ethylenically unsaturated compounds.

7 Claims, No Drawings

PLATINUM COMPLEXES HAVING FERROCENE LIGANDS FOR THE CATALYSIS OF THE ALKOXYCARBONYLATION OF ETHYLENICALLY UNSATURATED COMPOUNDS

The present invention relates to platinum complexes having ferrocene ligands for the catalysis of the alkoxycarbonylation of ethylenically unsaturated compounds.

The alkoxycarbonylation of ethylenically unsaturated compounds is a process of increasing significance. An alkoxycarbonylation is understood to mean the reaction of ethylenically unsaturated compounds such as olefins with carbon monoxide and alcohols in the presence of a metal or a metal complex and a ligand to give the corresponding esters:

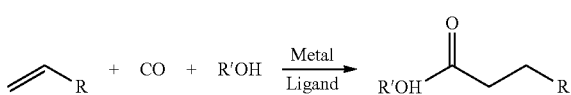

Scheme 1: General reaction equation of the alkoxycarbonylation of an ethylenically unsaturated compound EP 0 662 467 A1 describes a method of alkoxycarbonylation. The complexes described therein, as well as the ligands, have palladium as central atom.

A disadvantage of palladium is its high cost.

The technical problem addressed by the present invention is that of providing novel complexes having a less costly metal than palladium as the central atom. The complex is additionally to achieve good conversions in alkoxycarbonylations.

This object is achieved by a complex according to Claim 1.

Complex comprising Pt and a compound of formula (I)

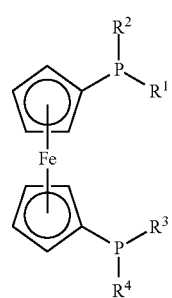

(I)

where
R$^1$, R$^2$, R$^3$, R$^4$ are each independently selected from —(C$_1$-C$_{12}$)-alkyl, —(C$_1$-C$_{12}$)-cycloalkyl, —(C$_3$-C$_{12}$)-heterocycloalkyl, —(C$_6$-C$_{20}$)-aryl, —(C$_6$-C$_{20}$)-heteroaryl;
at least one of the R$^1$, R$^2$, R$^3$, R$^4$ radicals is a —(C$_6$-C$_{20}$)-heteroaryl radical having at least six ring atoms;
and
R$^1$, R$^2$, R$^3$, R$^4$, if they are —(C$_1$-C$_{12}$)-alkyl, —(C$_1$-C$_{12}$)-cycloalkyl, —(C$_3$-C$_2$)-heterocycloalkyl, —(C$_6$-C$_{20}$)-aryl or —(C$_6$-C$_{20}$)-heteroaryl,
may each independently be substituted by one or more substituents selected from: —(C$_1$-C$_{12}$)-alkyl, —O—(C$_1$-C$_{12}$)-alkyl, —OH, —NH$_2$, halogen.

The expression (C$_1$-C$_{12}$)-alkyl encompasses straight-chain and branched alkyl groups having 1 to 12 carbon atoms. These are preferably (C$_1$-C$_8$)-alkyl groups, more preferably (C$_1$-C$_6$)-alkyl, most preferably (C$_1$-C$_4$)-alkyl.

The expression (C$_3$-C$_{12}$)-cycloalkyl encompasses mono-, bi- or tricyclic hydrocarbyl groups having 3 to 12 carbon atoms. Preferably, these groups are (C$_3$-C$_{12}$)-cycloalkyl.

The expression (C$_3$-C$_2$)-heterocycloalkyl encompasses nonaromatic, saturated or partly unsaturated cycloaliphatic groups having 3 to 12 carbon atoms, where one or more of the ring carbon atoms are replaced by heteroatoms. The —(C$_3$-C$_{12}$)-heterocycloalkyl groups have preferably 3 to 8, more preferably 5 or 6, ring atoms. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N.

The expression (C$_6$-C$_{20}$)-aryl encompasses mono- or polycyclic aromatic hydrocarbyl radicals having 6 to 20 carbon atoms. These are preferably (C$_6$-C$_{14}$)-aryl, more preferably (C$_1$-C$_{10}$)-aryl.

The expression (C$_6$-C$_{20}$)-heteroaryl encompasses mono- or polycyclic aromatic hydrocarbyl radicals having 6 to 20 carbon atoms, where one or more of the carbon atoms are replaced by heteroatoms. Preferred heteroatoms are N, O and S. The (C$_6$-C$_{20}$)-heteroaryl groups have 6 to 20, preferably 6 to 14 and more preferably 6 to 10 ring atoms. Thus, for example, pyridyl in the context of this invention is a C$_6$-heteroaryl radical; furyl is a C$_5$-heteroaryl radical.

Suitable (C$_6$-C$_{20}$)-heteroaryl groups having at least six ring atoms are especially pyridyl, pyridazinyl, pyrimidyl, pyrazinyl, benzofuranyl, indolyl, isoindolyl.

The expression halogen especially encompasses fluorine, chlorine, bromine and iodine. Particular preference is given to fluorine and chlorine.

In one embodiment, at least two of the R$^1$, R$^2$, R$^3$, R$^4$ radicals are a —(C$_6$-C$_{20}$)-heteroaryl radical having at least six ring atoms.

In one embodiment, the R$^1$ and R$^3$ radicals are each a —(C$_6$-C$_{20}$)-heteroaryl radical having at least six ring atoms.

In one embodiment, the R$^1$ and R$^3$ radicals are each 2-pyridyl.

In one embodiment, R$^2$ and R$^4$ are —(C$_1$-C$_{12}$)-alkyl.

In one embodiment, R$^2$ and R$^4$ are tert-butyl.

In one embodiment, the compound (I) has the structure (1):

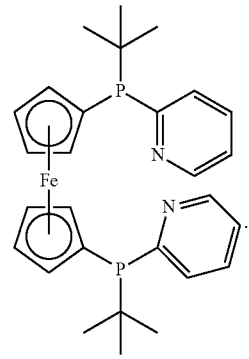

(1)

The invention further relates to the use of a complex according to the invention for catalysis of an alkoxycarbonylation reaction.

Process comprising the process steps of
a) initially charging an ethylenically unsaturated compound;
b) adding an above-described complex, or
   a compound of formula (I)

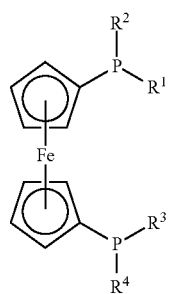

(I)

where
R$^1$, R$^2$, R$^3$, R$^4$ are each independently selected from —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl, —(C$_6$-C$_{20}$)-heteroaryl;
at least one of the R$^1$, R$^2$, R$^3$, R$^4$ radicals is a —(C$_6$-C$_{20}$)-heteroaryl radical having at least six ring atoms;
and
R$^1$, R$^2$, R$^3$, R$^4$, if they are —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl or —(C$_6$-C$_{20}$)-heteroaryl,
may each independently be substituted by one or more substituents selected from: —(C$_1$-C$_{12}$)-alkyl, —O—(C$_1$-C$_{12}$)-alkyl, —OH, —NH$_2$, halogen, and
a substance comprising Pt;
c) adding an alcohol;
d) feeding in CO;
e) heating the reaction mixture from a) to d), with conversion of the ethylenically unsaturated compound to an ester.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in in two or more steps, in such a way that, for example, a portion of the CO is first fed in, then the mixture is heated, and then a further portion of CO is fed in.

The ethylenically unsaturated compounds used as reactant in the process according to the invention contain one or more carbon-carbon double bonds. These compounds are also referred to hereinafter as olefins for simplification. The double bonds may be terminal or internal.

The ethylenically unsaturated compounds may, in addition to the one or more double bonds, contain further functional groups. At the same time, the ethylenically unsaturated compound preferably comprises a total of 2 to 30 carbon atoms, preferably 2 to 22 carbon atoms, more preferably 2 to 12 carbon atoms.

In one variant of the process, the ethylenically unsaturated compound does not comprise any further functional groups apart from carbon-carbon double bonds.

In one variant of the process, the ethylenically unsaturated compound is selected from: ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, or mixtures thereof.

In one variant of the process, the ethylenically unsaturated compound is selected from: propene, 1-butene, cis-2-butene, trans-2-butene, or mixtures thereof.

In one variant of the process, the ethylenically unsaturated compound is selected from: 1-pentene, cis-2-pentene, trans-2-pentene, 2-methyl-1-butene, 2-methyl-2-butene, 3-methyl-1-butene, or mixtures thereof.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate II is a portion of the C$_4$ fraction which arises in naphtha cracking and consists essentially of the isomeric n-butenes, isobutane and n-butane after removal of isobutene from raffinate I. Raffinate III is a portion of the C$_4$ fraction which arises in naphtha cracking and consists essentially of the isomeric n-butenes and n-butane.

In one variant, a mixture comprising isobutene, 1-butene, cis- and trans-2-butene is used. Preferably, the mixture comprises 1-butene, cis- and trans-2-butene.

In one variant of the process, the alcohol in process step c) is selected from: methanol, ethanol, 1-propanol, 1-butanol, 1-pentanol, 1-hexanol, 2-propanol, tert-butanol, 3-pentanol, cyclohexanol, phenol.

In one variant of the process, the alcohol in process step c) is methanol.

In one variant of the process, the substance comprising Pt is selected from: platinum dichloride (PtCl$_2$), platinum(II) acetylacetonate [Pt(acac)$_2$], platinum(II) acetate [Pt(OAc)$_2$], dichloro(1,5-cyclooctadiene)platinum(II) [Pt(cod)$_2$Cl$_2$], bis(dibenzylideneacetone)platinum [Pt(dba)$_2$], bis(acetonitrile)dichloroplatinum(II) [Pt(CH$_3$CN)$_2$Cl$_2$], (cinnamyl)platinum dichloride [Pt(cinnamyl)Cl$_2$].

In one variant of the process, the substance comprising Pt is selected from: platinum dichloride (PtCl$_2$), platinum(II) acetylacetonate [Pt(acac)$_2$], platinum(II) acetate [Pt(OAc)$_2$].

CO is fed in in step d) preferably at a partial CO pressure between 0.1 and 10 MPa (1 to 100 bar), preferably between 1 and 8 MPa (10 to 80 bar), more preferably between 2 and 6 MPa (20 to 60 bar).

The reaction mixture is heated in step e) of the process according to the invention preferably to a temperature in the range from 60° C. to 160° C., preferably in the range from 80 to 140° C., more preferably in the range from 100 to 140° C., in order to convert the ethylenically unsaturated compound to an ester.

The invention is to be illustrated in detail hereinafter by a working example.

Conversion of 1-octene to the Methyl Ester

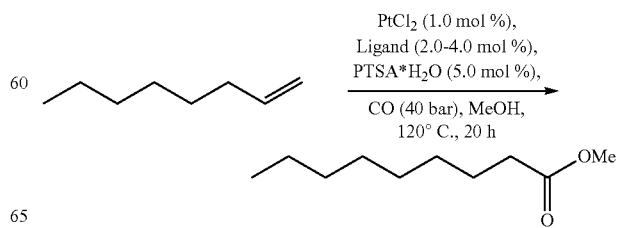

Reaction conditions: 1-Octene (1.0 mmol), PtCl$_2$ (0.01 mmol, 1.0 mol %), ligand: monodentate phosphine ligand (0.04 mmol, 4.0 mol %), bidentate phosphine ligand (0.02 mmol, 2.0 mol %), PTSA·H$_2$O (monohydrate of p-toluenesulfonic acid) (5.0 mol %), MeOH (2.0 ml), pressure (CO): 40 bar, temperature: 120° C., reaction time: 20 h.

The reaction was conducted with the following ligands:

Monodentate phosphine ligands:

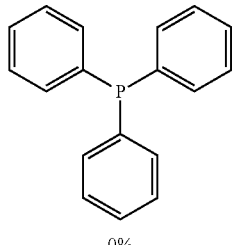

L1

0%

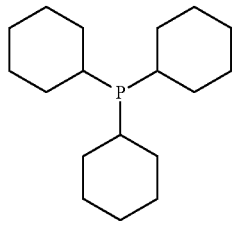

L2

0%

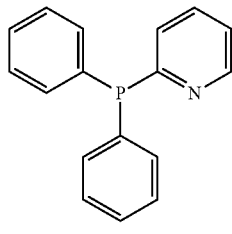

L3

0%

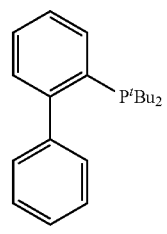

L4

0%

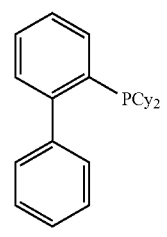

L5

0%

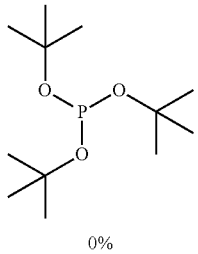

L6

0%

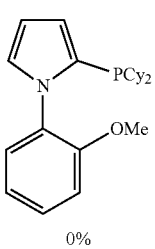

L7

0%

Bidentate phosphine ligands:

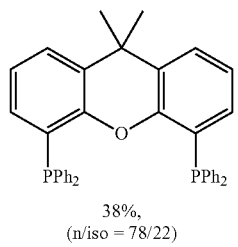

L8

38%,
(n/iso = 78/22)

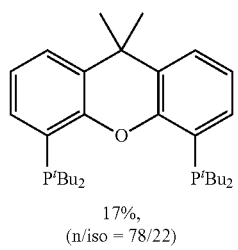

L9

17%,
(n/iso = 78/22)

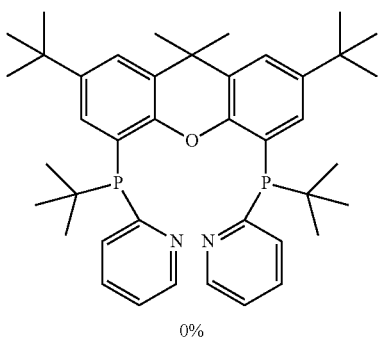

L10

0%

-continued

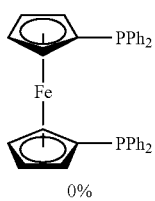

0%

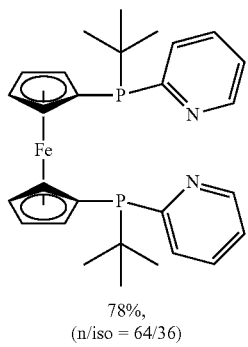

78%,
(n/iso = 64/36)

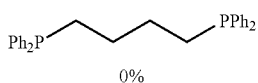

0%

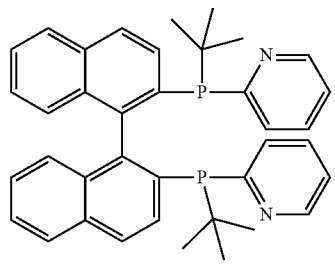

54%,
(n/iso = 73/27)

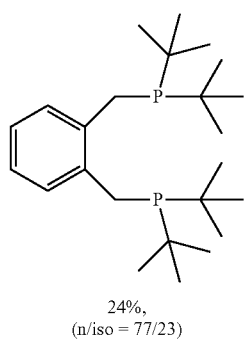

24%,
(n/iso = 77/23)

-continued

L11

L12

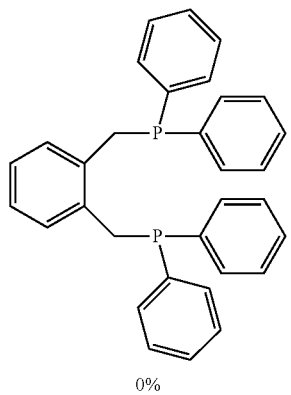

0%

The respective yield and n/iso selectivity are stated below the ligand. Selectivities and yields were determined by gas chromatography with mesitylene as internal standard.

Of the 16 ligands used, 11 did not give any conversion (0%). Only with one ligand (L12=(1)) was it possible to achieve a conversion of more than 60%. As shown by the series experiments, the greatest conversion is achieved with the inventive complex of Pt and (1).

The cost of Pt is below that of Pd. The object is thus achieved by a complex according to the invention.

L13

The invention claimed is:

1. Complex comprising Pt and a compound of formula (I)

L14

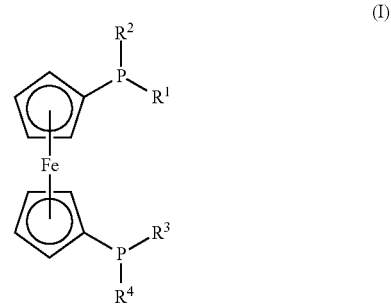

(I)

L15 where
R$^1$, R$^2$, R$^3$, R$^4$ are each independently selected from —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl, —(C$_6$-C$_{20}$)-heteroaryl;
at least one of the R$^1$, R$^2$, R$^3$, R$^4$ radicals is a —(C$_6$-C$_{20}$)-heteroaryl radical having at least six ring atoms;
and
R$^1$, R$^2$, R$^3$, R$^4$, if they are —(C$_1$-C$_{12}$)-alkyl, —(C$_3$-C$_{12}$)-cycloalkyl, —(C$_3$-C$_{12}$)-heterocycloalkyl, —(C$_6$-C$_{20}$)-aryl or —(C$_6$-C$_{20}$)-heteroaryl,
may each independently be substituted by one or more substituents selected from: —(C$_1$-C$_{12}$)-alkyl, —O—(C$_1$-C$_{12}$)-alkyl, —OH, —NH$_2$, halogen.

2. The complex according to claim 1,
wherein at least two of the R$^1$, R$^2$, R$^3$, R$^4$ radicals are a —(C$_6$-C$_{20}$)-heteroaryl radical having at least six ring atoms.

3. The complex according to claim 1,
wherein the R$^1$ and R$^3$ radicals are each a —(C$_6$-C$_{20}$)-heteroaryl radical having at least six ring atoms.

4. The complex according to claim 1,
wherein the $R^1$ and $R^3$ radicals are each 2-pyridyl.
5. The complex according to claim 1,
wherein $R^2$ and $R^4$ are —$(C_1$-$C_{12})$-alkyl.
6. The complex according to claim 1,
wherein $R^2$ and $R^4$ are tert-butyl.
7. The complex according to claim 1,
wherein the compound (I) has the structure (1):
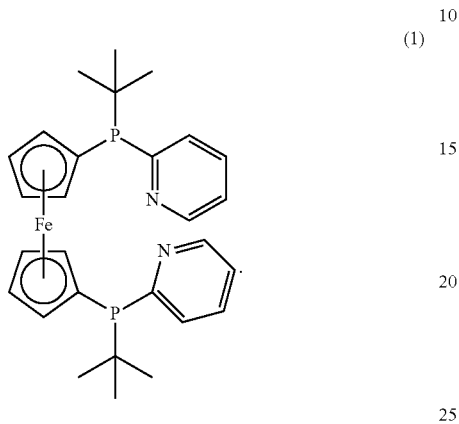
(1)
* * * * *